United States Patent [19]
Berg

[11] Patent Number: 5,160,585
[45] Date of Patent: Nov. 3, 1992

[54] SEPARATION OF TETRACHLOROETHYLENE FROM A BUTYL ALCOHOL BY EXTRACTIVE DISTILLATION

[75] Inventor: Lloyd Berg, 1314 S. 3rd Ave., Bozeman, Mont. 59715

[73] Assignee: Lloyd Berg, Bozeman, Mont.

[21] Appl. No.: 734,606

[22] Filed: Jul. 23, 1991

[51] Int. Cl.$^5$ .................. B01D 3/40; C07C 17/38; C07C 29/84
[52] U.S. Cl. .................. 203/57; 203/58; 203/60; 203/62; 203/63; 203/64; 203/65; 568/913; 570/262
[58] Field of Search .................. 203/64, 63, 60, 62, 203/57, 58, 65; 570/262; 568/913, 918

[56] References Cited

U.S. PATENT DOCUMENTS 4,036,703  7/1977  Leroi et al. ............ 570/262
4,121,978  10/1978  Becuwe ................. 570/262

Primary Examiner—Wilbur Bascomb, Jr.

[57] ABSTRACT

Tetracholorethylene cannot be completely separated from n-butanol, isobutanol or 2-butanol by conventional distillation or rectification because of minimum boiling azeotropes. Tetrachloroethylene can be readily separated from n-butanol, isobutanol or 2-butanol by extractive distillatiion. Typical effective agents are: for n-butanol, dipropylene glycol methyl ether; for isobutanol, dimethylsulfoxide and isobutyl butyrate; for 2-butanol, ethylene glycol methyl ether and isobornyl acetate.

5 Claims, No Drawings

SEPARATION OF TETRACHLOROETHYLENE FROM A BUTYL ALCOHOL BY EXTRACTIVE DISTILLATION

FIELD OF THE INVENTION

This invention relates to a method for separating tetrachloroethylene from the butyl alcohols using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Tetrachloroethylene, B.P.=121° C. forms minimum boiling azeotropes with three of the butyl alcohols. With n-butanol the azeotrope boils at 109° C. and contains 71 weight percent tetrachloroethylene; with isobutanol the azeotrope boils at 103° C. and contains 60% tetrachloroethylene and with 2-butanol the azeotrope boils at 97° C. and contains 68% tetrachloroethylene. There is no azeotrope with t-butanol. Extractive distillation would be an attractive method of effecting the separation of tetrachloroethylene from these alcohols if agents can be found that (1) will enhance the relative volatility between tetrachloroethylene and these alcohols and (2) are easy to recover, that is, form no azeotrope with tetrachloroethylene, n-butanol, isobutanol or 2-butanol and boil sufficiently above these four compounds to make separation by rectification possible with only a few theoretical plates. Extractive distillation typically requires the addition of an equal amount to twice as much extractive agent as the tetrachloroethylene-butanol on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the tetrachloroethylene and alcohols otherwise it will form a two phase azeotrope with it and some other method of separation will have to be employed.

TABLE 1

Effect of Relative Volatility on the Separation of Tetrachloroethylene From Butanols at 99% Purity.

| Relative Volatility | Theoretical Plates | Actual Plates, 75% Efficiency | Actual Plates, 75% Eff., Min. Reflux |
| --- | --- | --- | --- |
| 1.2 | 50 | 67 | 87 |
| 1.3 | 35 | 47 | 61 |
| 1.4 | 27 | 36 | 47 |
| 1.5 | 23 | 31 | 40 |
| 1.6 | 20 | 27 | 35 |
| 1.7 | 17 | 23 | 29 |

The advantage of employing an effective extractive distillation agent is shown in Table 1. Tetrachloroethylene forms minimum boiling azeotropes with the butyl alcohols which possess a relative volatility of 1.0 and cannot be separated by rectification. If extractive distillation is employed with an agent yielding a relative volatility of 1.7 or higher, a rectification column of only 29 actual plates will be required.

OBJECTIVE OF THE INVENTION

The objects of this invention are to provide a process or method of extractive distillation that will enhance the relative volatility of tetrachloroethylene to n-butanol, isobutanol or 2-butanol in their separation in a rectification column. It is a further object of this invention to identify organic compounds that are stable, can be separated from the tetrachloroethylene or the alcohols by rectification with relatively few plates and can be recycled to the extractive distillation column with little decomposition.

SUMMARY OF THE INVENTION

The objects of this invention are provided by a process for the separation of tetrachloroethylene from n-butanol, isobutanol or 2-butanol which entails the use of certain organic compounds as the agent in extractive distillation.

DETAILED DESCRIPTION OF THE INVENTION

I have discovered that certain organic compounds will effectively increase the relative volatility between tetrachloroethylene and n-butanol, isobutanol or 2-butanol by rectification when when employed as the agent in extractive distillation. Table 2 lists the compounds that I have found to be effective extractive distillation agents to recover tetrachloroethylene from n-butanol. The data in Tables 2,3,5,6,8 and 9 was obtained in a vapor-liquid equilibrium still. In every case, the starting mixture was the tetrachloroethylene-butanol azeotrope. The relative volatilities are listed for each of the agents. The compounds which are effective extractive distillation agents to remove tetrachloroethylene from n-butanol are dipropylene glycol methyl ether, diethylene glycol ethyl ether, 1-methoxy-2-propanol, ethyl 3-ethoxypropionate, butoxypropanol, diethylene glycol methyl ether, 1-methoxy-2-propanol acetate, ethylene glycol butyl ether, ethylene glycol methyl ether, ethylene glycol ethyl ether, diethylene glycol butyl ether, propylene glycol methyl ether, propylene glycol isobutyl ether, 4-methoxy-4-methyl pentanone-2, ethylene glycol phenyl ether, propoxypropanol and mesityl oxide.

Table 3 lists the agents that were found to be ineffective agents for separating tetrachloroethylene from n-butanol.

One of the agents, dipropylene glycol methyl ether, whose relative volatility had been determined in the vapor-liquid equilibrium still, was then evaluated in a glass perforated plate rectification column possessing 7.3 theoretical plates and the results listed in Table 4. Dipropylene glycol methyl ether gave a relative volatility of 1.72 after two hours of operation.

Table 5 lists the compounds that I have found to be effective extractive distillation agents to recover tetrachloroethylene from isobutanol. The effective agents are ethyl valerate, ethyl isovalerate, ethyl butyrate, n-amyl acetate, hexyl formate, 4-methylpentyl acetate-2, 2-ethyl hexyl acetate, methyl caproate, methyl benzoate, ethyl benzoate, ethylene glycol butyl ether acetate, isobutyl butyrate, isobutyl isobutyrate, 1-methoxy-2-propanol acetate, 3-heptanone, isobutyl heptyl ketone, dimethylsulfoxide, dimethylformamide, dimethylacetamide, sulfolane and acetophenone. The starred compounds in Table 5 bring the tetrachloroethylene out as overhead product; the others bring out isobutanol as overhead.

TABLE 2

Effective Agents For Separating Tetrachloroethylene From n-Butanol

| Compounds | Relative Volatility |
|---|---|
| Diethylene glycol ethyl ether | 1.5 |
| 1-Methoxy-2-propanol | 2.2 |
| Ethyl 3-ethoxypropionate | 2.8 |
| Butoxypropanol | 1.45 |
| Dipropylene glycol methyl ether | 1.7 |
| Diethylene glycol methyl ether | 1.8 |
| 1-Methoxy-2-propanol acetate | 2.0 |
| Ethylene glycol butyl ether | 1.35 |
| Ethylene glycol methyl ether | 2.4 |
| Ethylene glycol ethyl ether | 2.2 |
| Diethylene glycol butyl ether | 1.65 |
| Propylene glycol methyl ether | 2.1 |
| Propylene glycol isobutyl ether | 1.75 |
| 4-Methoxy-4-methyl pentanone-2 | 1.5 |
| Ethylene glycol phenyl ether | 1.45 |
| Propoxypropanol | 1.2 |
| Mesityl oxide | 1.25 |

TABLE 3

Ineffective Agents, Tetrachloroethylene - n-Butanol

| | |
|---|---|
| Hexyl acetate | Dipropylene glycol methyl ether acetate |
| Methyl isoamyl ketone | Ethylene glycol ethyl ether acetate |
| 2-Methoxy-2-propanol acetate | 4-Methoxy-2-pentanone |
| 2,6-Dimethyl-4-heptanone | Diisobutyl ketone |
| 3-Heptanone | Ethyl isovalerate |
| 2-Methoxyethyl ether | Ethylene glycol hexyl ether |
| Dipropylene glycol dimethyl ether | |

TABLE 4

Data From Run Made In Rectification Column

| Agent | Column | Time hrs. | Weight % $C_2Cl_4$ | Weight % n-Butanol | Relative Volatility |
|---|---|---|---|---|---|
| Dipropylene glycol methyl ether | Overhead | 1 | 85.1 | 14.9 | 1.2 |
| | Bottoms | | 60.4 | 39.6 | |
| Dipropylene glycol methyl ether | Overhead | 2 | 98.9 | 1.1 | 1.72 |
| | Bottoms | | 62.2 | 37.8 | |

TABLE 5

Effective Agents For Separating Tetrachloroethylene From Isobutanol

| Compounds | Relative Volatility |
|---|---|
| Ethyl valerate | 1.4 |
| Ethyl isovalerate | 1.55 |
| Ethyl butyrate | 2.9 |
| n-Amyl acetate | 1.3 |
| Hexyl formate | 1.3 |
| 4-Methyl pentyl acetate-2 | 2.6 |
| Ethyl hexyl acetate | 1.25 |
| Methyl caproate | 1.5 |
| Methyl benzoate | 1.3 |
| Ethyl benzoate | 1.25 |
| Ethylene glycol butyl ether acetate | 1.25 |
| Isobutyl butyrate | 1.55 |
| Isobutyl isobutyrate | 1.25 |
| 1-Methoxy-2-propanol acetate | 1.55* |
| 3-Heptanone | 1.25 |
| Isobutyl heptyl ketone | 1.35 |
| Dimethylsulfoxide | 2.3* |
| Dimethylformamide | 2.3* |
| Dimethylacetamide | 1.7* |
| Sulfolane | 1.2* |
| Acetophenone | 1.4 |

*Brings out tetrachloroethylene as overhead

TABLE 6

Ineffective Agents, Tetrachloroethylene - Isobutanol

| | |
|---|---|
| n-Decanol | Nonyl alcohol |
| n-Octanol | Isophorone |
| Benzyl alcohol | Ethylene glycol ethyl ether acetate |
| Hexyl acetate | Ethyl-3-ethoxypropionate |
| Isobornyl acetate | Ethylene glycol diacetate |
| Ethyl acetoacetate | 5-Methyl-2-hexanone |
| 2-Heptanone | Ethyl phenyl acetate |
| 2-Octanone | 2-Undecanone |
| Nitromethane | Nitroethane |

TABLE 7

Data From Run Made In Rectification Column

| Agent | Column | Time hrs. | Weight % $C_2Cl_4$ | Weight % Isobutanol | Relative Volatility |
|---|---|---|---|---|---|
| Dimethylsulfoxide | Overhead | 1 | 99.5 | 0.5 | 2.2 |
| | Bottoms | | 33.9 | 66.1 | |
| Dimethylsulfoxide | Overhead | 2 | 99.6 | 0.4 | 2.3 |
| | Bottoms | | 38.0 | 62.0 | |

Table 6 lists the agents that were found to be ineffective agents for separating tetrachloroethylene from isobutanol.

Dimethylsulfoxide, whose relative volatility had been determined in the vapor-liquid equilibrium still, was evaluated in the perforated plate rectification column and the results listed in Table 7. Dimethylsulfoxide gave a relative volatility of 2.3 after two hours of operation.

Table 8 lists the compounds that I have found to be effective extractive distillation agents to recover tetrachloroethylene from 2-butanol. The effective agents are ethyl valerate, ethyl isovalerate, isobutyl butyrate, isobutyl isobutyrate, ethyl butyrate, hexyl formate, isobornyl acetate, diethylene glycol hexyl ether, ethylene glycol ethyl ether acetate, 4-methyl pentyl axetate-2, ethylene glycol methyl ether, ethylene glycol ethyl ether, ethylene glycol hexyl ether, diethylene glycol methyl ether, 4-methyl-2-pentanone, isophorone, dipropylene glycol methyl ether acetate and hexyl acetate. The starred compounds in Table 8 bring out tetrachloroethylene as overhead product; the others bring out 2-butanol as overhead product.

Table 9 lists agents that were found to be ineffective for separating tetrachloroethylene from 2-butanol.

Isobornyl acetate, whose relative volatility had been determined in the vapor-liquid equilibrium still, was evaluated in the perforated plate rectification column and the results listed in Table 10. Isobornyl acetate gave a relative volatility of 1.39 after one hours of operation.

THE USEFULNESS OF THE INVENTION

The usefulness or utility of this invention can be demonstrated by referring to the data presented in Tables 2 to 10. All of the successful agents show that tetrachloroethylene can be separated from n-butanol, isobutanol or 2-butanol by means of extractive distillation in a rectification column and that the ease of separation as measured by relative volatility is considerable.

WORKING EXAMPLES

EXAMPLE 1

Seventy grams of the tetrachloroethylene-n-butanol azeotrope and 30 grams of dipropylene glycol methyl ether were charged to a vapor-liquid equilibrium still and refluxed for six hours. Analysis indicated a vapor composition of 64.6% tetrachloroethylene, 35.4% n-butanol; a liquid composition of 50% tetrachloroethylene, 50% n-butanol which is a relative volatility of tetrachloroethylene to n-butanol of 1.8.

TABLE 8

| Effective Agents For Separating Tetrachloroethylene From 2-Butanol | |
|---|---|
| Compounds | Relative Volatility |
| Ethyl valerate | 1.85 |
| Isobutyl butyrate | 1.5 |
| Ethyl isovalerate | 1.85 |
| Isobutyl isobutyrate | 1.55 |
| Ethyl butyrate | 1.35 |
| Hexyl formate | 1.3 |
| Isobornyl acetate | 1.4 |
| Diethylene glycol hexyl ether | 1.25 |
| Ethylene glycol ethyl ether acetate | 1.4 |
| 4-Methyl pentyl acetate-2 | 1.25 |
| Ethylene glycol methyl ether | 1.3* |
| Ethylene glycol ethyl ether | 1.2* |
| Ethylene glycol hexyl ether | 1.2* |
| Diethylene glycol methyl ether | 1.2* |
| 4-Methyl-2-pentanone | 1.2* |
| Isophorone | 1.2* |
| Dipropylene glycol methyl ether acetate | 1.2* |
| Hexyl acetate | 1.35 |

*Brings out tetrachloroethylene as overhead

TABLE 9

| Ineffective Agents, Tetrachloroethylene - 2-Butanol | |
|---|---|
| Ethylene glycol butyl ether | Diethylene glycol ethyl ether |

TABLE 9-continued

| Ineffective Agents, Tetrachloroethylene - 2-Butanol | |
|---|---|
| Diethylene glycol butyl ether | Dipropylene glycol methyl ether |
| Propylene glycol methyl ether | Propylene glycol isobutyl ether |
| Propoxypropanol | Tripropylene glycol methyl ether |
| Butoxypropanol | 1-Methoxy-2-propanol acetate |
| Cyclohexanol | 2-Ethyl hexyl acetate |
| Methyl benzoate | Diethyl maleate |
| Ethyl benzoate | |

TABLE 10

| Data From Run Made In Rectification Column | | | | | |
|---|---|---|---|---|---|
| Agent | Column | Time hrs. | Weight % $C_2H_4$ | Weight % 2-Butanol | Relative Volatility |
| Isobornyl acetate | Overhead | 1 | 6.1 | 93.9 | 1.39 |
| | Bottoms | | 41.5 | 58.5 | |

EXAMPLE 2

A solution comprising 140 grams of tetrachloroethylene and 60 grams of n-butanol was placed in the stillpot of a 7.3 theoretical plate rectification column. When refluxing began, an extractive agent comprising dipropylene glycol methyl ether was pumped into the column at a rate of 15 ml/min. The temperature of the extractive agent as it entered the column was 85° C. After establishing the feed rate of the extractive agent, the heat input to the tetrachloroethylene-n-butanol in the stillpot was adjusted to give a total reflux rate of 40 ml/min. After two hours of operation, overhead and bottoms samples were collected and analysed. The overhead analysis was 98.9% tetrachloroethylene, 1.1% n-butanol and the bottoms analysis was 62.2% tetrachloroethylene, 37.8% n-butanol. This gives an average relative volatility of 1.72 for each theoretical plate. This data is presented in Table 4.

EXAMPLE 3

Seventy grams of the tetrachloroethylene-isobutanol azeotrope and 30 grams of dimethylsulfoxide were charged to the vapor-liquid equilibrium still and refluxed for five hours. Analysis indicated a vapor composition of 59.1% tetrachloroethylene, 40.9% isobutanol; a liquid composition of 36.6% tetrachloroethylene, 63.4% isobutanol which is a relative volatility of tetrachloroethylene to isobutanol of 2.5.

EXAMPLE 4

A solution comprising 180 grams of tetrachloroethylene and 120 grams of isobutanol was placed in the stillpot of a 7.3 theoretical plate rectification column. When refluxing began, an extractive agent comprising dimethylsulfoxide was pumped into the column at a rate of 15 ml/min. The temperature of the extractive agent as it entered the column was 85° C. After establishing the feed rate of the extractive agent, the heat input to the tetrachloroethylene-isobutanol in the stillpot was adjusted to give a total reflux rate of 40 ml/min. After two hours of operation, the overhead and bottoms were collected and analysed. The overhead analysis was 99.6% tetrachloroethylene, 0.4% isobutanol and the bottoms analysis was 38% tetrachloroethylene, 62% isobutanol. This gives an average relative volatility of 2.3 for each theoretical plate. This data is presented in Table 7.

EXAMPLE 5

Seventy grams of the tetrachloroethylene-2-butanol azeotrope and 30 grams of isobornyl acetate were charged to the vapor-liquid equilibrium still and refluxed for seven hours. Analysis indicated a vapor composition of 72.5% 2-butanol, 27.5% tetrachloroethylene; a liquid composition of 65% 2-butanol, 35% tetrachloroethylene which is a relative volatility of 2-butanol to tetrachloroethylene of 1.7.

EXAMPLE 6

A solution comprising 150 grams of tetrachloroethylene and 100 grams of 2-butanol was placed in the stillpot of a 7.3 theoretical plate rectification column. When refluxing began, an extractive agent comprising isobornyl acetate was pumped into the column at a rate of 15 ml/min. The temperature of the extractive agent as it entered the column was 85° C. After establishing the feed rate of the extractive agent, the heat input to the tetrachloroethylene-2-butanol in the stillpot was adjusted to give a total reflux rate of 40 ml/min. After one hour of operation, the overhead and bottoms samples were collected and analysed. The overhead analysis was 93.9% 2-butanol, 6.1% tetrachloroethylene and the bottoms analysis was 58.5% 2-butanol, 41.5% tetrachloroethylene. This gives an average relative volatility of 2-butanol to tetrachloroethylene of 1.39 for each theoretical plate. This data is presented in Table 10.

I claim:

1. A method for recovering tetrachloroethylene from a mixture of tetrachloroethylene and n-butanol which comprises distilling a mixture of tetrachloroethylene and n-butanol in the presence of about one part of an extractive agent per part of tetrachloroethylene-n-butanol mixture, recovering the tetrachloroethylene as overhead product and obtaining the n-butanol and the extractive agent from the stillpot, wherein said extractive agent consists of one material selected from the group consisting of diethylene glycol ethyl ether, 1-methoxy-2-propanol, ethyl 3-ethoxypropionate, butoxypropanol, dipropylene glycol methyl ether, diethylene glycol methyl ether, 1-methoxy-2-propanol acetate, ethylene glycol butyl ether, ethylene glycol methyl ether, ethylene glycol ethyl ether, diethylene glycol butyl ether, propylene glycol methyl ether, propylene glycol isobutyl ether, ethylene glycol phenyl ether, 4-methoxy-4-methyl pentanone-2, propoxypropanol and mesityl oxide.

2. A method for recovering tetrachloroethylene from a mixture of tetrachloroethylene and isobutanol which comprises distilling a mixture of tetrachloroethylene and isobutanol in the presence of about one part of an extractive agent per part of tetrachloroethylene-isobutanol mixture, recovering tetrachloroethylene as overhead product and obtaining the isobutanol and the extractive agent from the stillpot, wherein said extractive agent consists of one material selected from the group consisting of 1-methoxy-2-propanol acetate, dimethylsulfoxide, dimethylformamide, dimethylacetamide and sulfolane.

3. A method for recovering isobutanol from a mixture of isobutanol and tetrachloroethylene which comprises distilling a mixture of isobutanol and tetrachloroethylene in the presence of about one part of isobutanol-tetrachloroethylene mixture, recovering the isobutanol as overhead product and obtaining the tetrachloroethylene and the extractive agent from the stillpot, wherein said extractive agent consists of one material selected from the group consisting of ethyl isovalerate, ethyl butyrate, n-amyl acetate, hexyl formate, 4-methyl pentyl acetate-2, 2-ethyl hexyl acetate, methyl caproate, methyl benzoate, ethyl benzoate, ethylene glycol butyl ether acetate, isobutyl butyrate, isobutyl isobutyrate, 3-heptanone, isobutyl heptyl ketone and acetophenone.

4. A method for recovering tetrachloroethylene from a mixture of tetrachloroethylene and 2-butanol which comprises distilling a mixture of tetrachloroethylene and 2-butanol in the presence of about one part of an extractive agent per part of tetrachloroethylene-2-butanol mixture, recovering tetrachloroethylene as overhead product and obtaining the 2-butanol and the extractive agent from the stillpot, wherein said extractive agent consists of one material selected from the group consisting of ethylene glycol methyl ether, ethylene glycol ethyl ether, ethylene glycol hexyl ether, diethylene glycol methyl ether, 4-methyl-2-pentanone, isophorone and dipropylene glycol methyl ether acetate.

5. A method for recovering 2-butanol from a mixture of 2-butanol and tetrachloroethylene which comprises distilling a mixture of 2-butanol and tetrachloroethylene in the presence of about one part of 2-butanol-tetrachloroethylene mixture, recovering the 2-butanol as overhead product and obtaining the tetrachloroethylene and the extractive agent from the stillpot, wherein said extractive agent consists of one material selected from the group consisting of ethyl valerate, isobutyl butyrate, ethyl isovalerate, isobutyl isobutyrate, ethyl butyrate, hexyl formate, isobornyl acetate, diethylene glycol hexyl ether, ethylene glycol ethyl ether acetate, 4-methyl pentyl acetate-2, and hexyl acetate.

* * * * *